(12) United States Patent
Bibette et al.

(10) Patent No.: US 11,220,702 B2
(45) Date of Patent: Jan. 11, 2022

(54) METHOD FOR MONITORING A REACTION AND TO REACTION SYSTEM FOR IMPLEMENTING SAME

(71) Applicants: Centre National de la Recherche Scientifique, Paris (FR); Sorbonne Université, Paris (FR)

(72) Inventors: Jérôme Bibette, Paris (FR); Pascal Panizza, Noyal-sur-Vilaine (FR); Nicolas Bremond, Paris (FR); Fabien Bertholle, Montfermeil (FR); Jean Marie Baudry, Paris (FR); Larysa Baraban, Irvine, TX (US); Laurent Boitard, Paris (FR)

(73) Assignees: Centre National de la Recherche Scientifique, Paris (FR); Sorbonne Université, Paris (FR)

( * ) Notice: Subject to any disclaimer, the term of this patent is extended or adjusted under 35 U.S.C. 154(b) by 1085 days.

(21) Appl. No.: 14/504,893

(22) Filed: Oct. 2, 2014

(65) Prior Publication Data

US 2015/0087008 A1     Mar. 26, 2015

Related U.S. Application Data

(63) Continuation-in-part of application No. 14/003,002, filed as application No. PCT/IB2012/050478 on Feb. 1, 2012, now abandoned.

(30) Foreign Application Priority Data

Mar. 4, 2011 (FR) ...................................... 11 00659

(51) Int. Cl.
    *C12Q 1/02*      (2006.01)
(52) U.S. Cl.
    CPC ...................... *C12Q 1/02* (2013.01)
(58) Field of Classification Search
    CPC ........................................................ C12Q 1/02
    USPC ........................................................ 435/29
    See application file for complete search history.

(56) References Cited

U.S. PATENT DOCUMENTS

| | | | | |
|---|---|---|---|---|
| 2007/0068573 | A1* | 3/2007 | Cox | G01N 27/44769 137/1 |
| 2007/0183934 | A1* | 8/2007 | Diercks | B01L 3/502761 422/400 |
| 2009/0042319 | A1 | 2/2009 | De Guzman et al. | |
| 2012/0040472 | A1 | 2/2012 | Churski et al. | |

FOREIGN PATENT DOCUMENTS

| | | |
|---|---|---|
| WO | WO-2004/089533 | 10/2004 |
| WO | WO-2007/021818 | 2/2007 |

OTHER PUBLICATIONS

Clausell-Tormos et al. (Droplet-Based Microfluidic Platforms for the Encapsulation and Screening of Mammalian Cells and Multicellular Organisms. Chemistry & Biology 15, 427-437 2008).*
Atencia et al. (Capillary inserts in microcirculatory systems. Lab Chip 2006, 6, 575-577).*
Office Action for U.S. Appl. No. 14/003,002 dated Jun. 1, 2016.
Office Action for U.S. Appl. No. 14/003,002 dated Sep. 9, 2015.
Office Action for U.S. Appl. No. 14/003,002 dated Apr. 12, 2017.
Atencia, J., et al.; "*Controlled microfluidic interfaces*;" Nature, vol. 437; pp. 648-655; dated Sep. 29, 2005.
International Search Report and Written Opinion of the International Searching Authority for Application No. PCT/IB2012/050478, dated Apr. 24, 2012.

* cited by examiner

*Primary Examiner* — Sharmila G Landau
*Assistant Examiner* — Natalie M Moss
(74) *Attorney, Agent, or Firm* — Alston & Bird LLP

(57) ABSTRACT

A method for monitoring a reaction and a reaction system are provided. The reaction system includes at least one vessel for the reaction medium, which is in fluid communication with an injection tube; at least one vessel for a carrier fluid that is immiscible with the reaction medium, which is in fluid communication with a reaction tube; the injection tube being mounted so as to lead into the reaction tube such that individual drops of the reaction medium can be injected into the reaction tube and into the immiscible carrier fluid, so as to form a train of reaction chambers; at least one detector for monitoring a reaction; a means for classifying the reaction chambers; and at least one means for recirculating reaction chambers in front of at least one detector for monitoring a reaction.

19 Claims, 5 Drawing Sheets

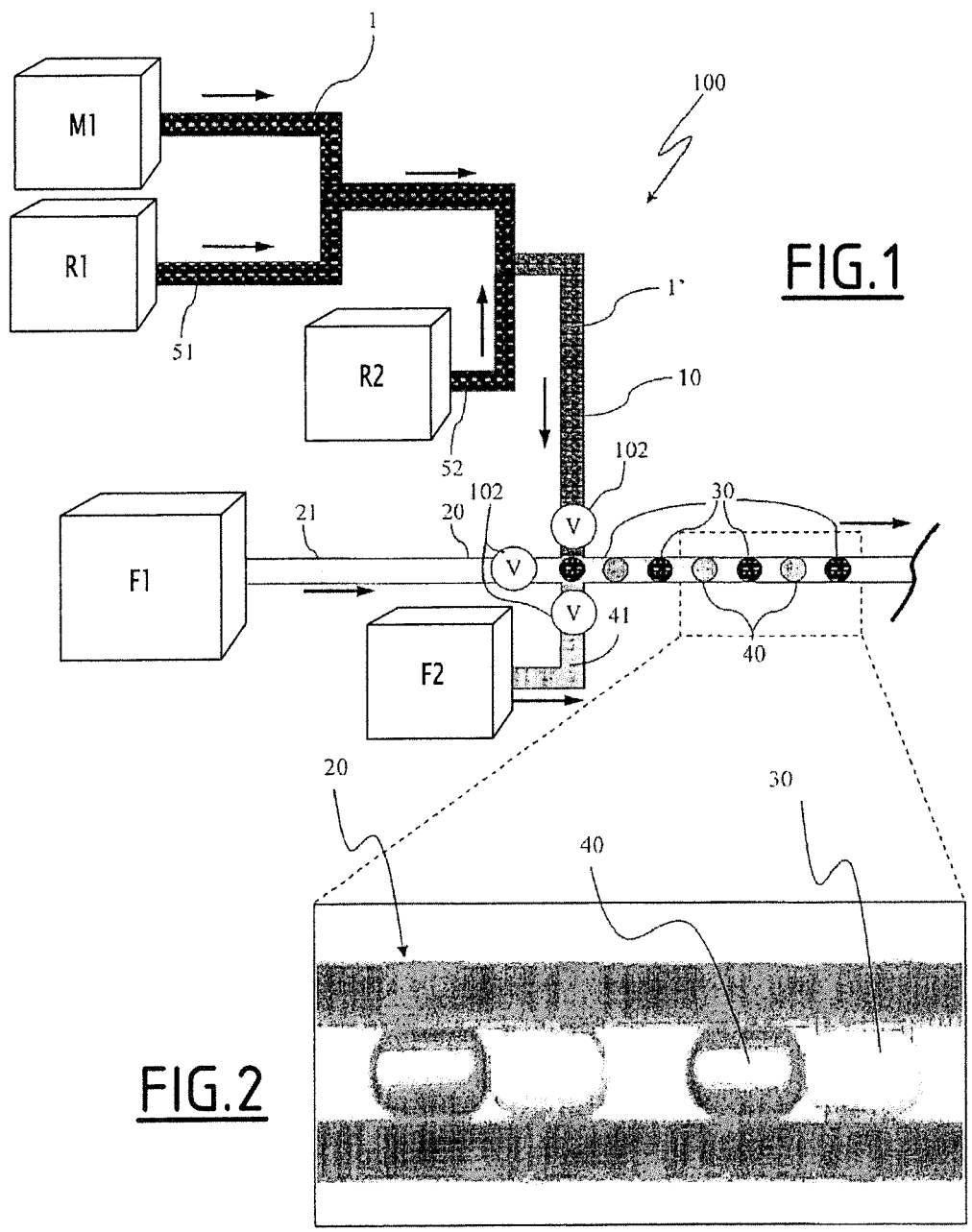

METHOD FOR MONITORING A REACTION AND TO REACTION SYSTEM FOR IMPLEMENTING SAME

CROSS REFERENCE TO RELATED APPLICATIONS

This application is a continuation-in-part of U.S. application Ser. No. 14/003,002, filed Nov. 14, 2013, which is a national stage application filed under 35 USC 371 of International Application No. PCT/IB2012/050478, filed Feb. 1, 2012, which claims priority from FR patent application 11 00659 filed Mar. 4, 2011, the entire contents of which are incorporated herein by reference.

FIELD

The invention relates to a method for monitoring a reaction and to a reaction system for application thereof.

This invention also concerns a method for monitoring reaction kinetics in a reaction medium between at least one component of the reaction medium and each of a plurality of different reagents.

BACKGROUND

The investigation of microbiological entities, such as unicellular or multicellular microorganisms, requires being able to detect a population of these microorganisms in one or more reactors, as well as the development of these microorganisms over time. It is also necessary to be able to select easily and extract the populations of interest.

There are now machines called "plate readers", which are in the form of plates equipped with a plurality of wells (currently up to 1536 on an area of 127.76×85.48 mm) arranged as a two-dimensional matrix, and in which the microorganisms are cultured in a given culture medium.

The first drawback of this type of machine is the need for a system for scanning in two dimensions so as to make the well that we wish to fill or analyze coincide with the appropriate tool (filling device or measuring equipment). A device of this kind is expensive, bulky and must be very accurate to ensure good coincidence between each well and the equipment.

Another major drawback is the need to take considerable precautions during manipulation of the plate to avoid causing plate vibration or spillage and creating contamination between the wells. Now, constant stirring of the wells is required to keep the medium homogeneous and in the case of microorganisms to prevent the formation of biofilms. This means that the amount of biomass attained or detectable in a well is limited.

Another drawback is the difficulty of controlling the evaporation of the culture medium in the wells, in view of the small volume of liquid contained in each well. One solution proposed is to keep the plate under controlled atmosphere and/or regularly supplement each well with culture medium to make up for the evaporation.

Such methods are tedious and can influence the growth of the microorganisms, inducing a bias in the experiments and the measurements.

In the article "Controlled microfluidic interfaces" (Atencia and Beebe, Nature Review, 437, 648-655, 2005), it has already been proposed to produce a reaction system comprising:
    several reservoirs of solutions of reagents fluidically connected to a capillary injection tube;
    at least one reservoir of a carrier fluid that is immiscible with the solutions of reagents, fluidically connected to a capillary reaction tube, the capillary injection tube being mounted opening into the capillary reaction tube so that individual drops of reagents can be injected into the capillary reaction tube, into the immiscible carrier fluid, so as to form a plurality of reactors.

This system makes it possible to carry out a large number of experiments in succession, notably for studying the factors involved in the crystallization of proteins. Once the measurement has been carried out (measurement of X-ray diffraction), the drops are transported to the end of the reaction tube and removed.

Another application consists of carrying out the encapsulation of therapeutic agents. Once said encapsulation has been performed, the drops are recovered at the outlet of the reaction tube and are packaged for use.

This system solves many problems with plate readers.

However, this system does not allow monitoring of reaction kinetics, in particular monitoring of the temporal evolution of a culture of living cells as well as sorting them. Furthermore, this method is limited to the study of a single reagent or a single mixture of reagents, such that the degree of automation of this method is limited.

SUMMARY

The present invention aims to solve the above drawbacks and proposes a reaction system, in particular for culturing microorganisms, that is economical, compact, easy to use, and allows complete control of the culture medium throughout the experiment, and monitoring of the reaction kinetics, in particular of the temporal evolution of a culture of living cells and sorting thereof.

For this, the invention proposes making a capillary reaction system, notably for culturing microorganisms, comprising a means of referencing the drops for identifying them uniquely in the succession of drops, and at least one means for recirculating the reactors in front of at least one reaction monitoring sensor.

For this purpose, the invention relates, according to a first aspect, to a reaction system, notably of cultures of microorganisms, comprising:
    at least one reservoir of reaction mixture fluidically connected to a capillary injection tube,
    at least one reservoir of a carrier fluid that is immiscible with the reaction mixture, fluidically connected to a capillary reaction tube,
    the capillary injection tube being mounted opening into the capillary reaction tube so that individual drops of reaction mixture can be injected into the capillary reaction tube, into the immiscible carrier fluid, so as to form a succession of reactors,
    at least one reaction monitoring detector.

The reaction system according to the invention comprises a means of referencing the reactors for identifying them uniquely in the succession of reactors, and at least one means for recirculating the reactors in front of at least one reaction monitoring detector.

According to other embodiments:
    the recirculating means can comprise a loop for recirculating the reactors in front of the detector or detectors, said recirculating loop comprising a capillary that discharges upstream and downstream of the detector or detectors;

the recirculating means can comprise a recirculating means that is able to reverse the direction of circulation of the reactors;

the reaction mixture can be a culture medium of microorganisms, the capillary reaction tube then being a capillary culture tube, and the reactors being reactors for culture of microorganisms;

the reaction system can further comprise at least one reservoir of a so-called "separating" fluid, immiscible with the carrier fluid and immiscible with the reaction mixture, fluidically connected to the capillary reaction tube so that drops of separating fluid can be injected into the carrier fluid between two reactors;

the reaction system can further comprise at least one reagent reservoir fluidically connected to the capillary injection tube and/or to the capillary reaction tube, so that reagent can be mixed with the reaction mixture;

the carrier fluid and the separating fluid can be mutually immiscible oils, the reaction mixture being an aqueous medium that is immiscible with the aforementioned oils;

the reaction system can further comprise at least one waste reservoir, connected fluidically to the capillary reaction tube;

the reaction system can further comprise at least one detector, the capillary reaction tube comprising at least one portion that is transparent to a signal emitted and/or detected by the detector;

the reaction system can further comprise a sampling capillary tube mounted opening into the capillary reaction tube so that at least one reactor can be sampled;

the reaction system can further comprise at least one diverting capillary tube mounted opening into the capillary reaction tube so that at least one reactor can be diverted to a means for treatment of one or more reactors;

the reaction system can further comprise a central control unit connected to the circulating means and capable of:
☐controlling the injection of individual drops of reaction mixture into the capillary reaction tube, in the carrier fluid, imposing a velocity and a duration of circulation of the reaction medium, so as to form a plurality of reactors;

controlling the circulation of the carrier fluid by imposing a velocity, duration and direction of circulation of the carrier fluid in the capillary reaction tube;

counting the reactors in the carrier medium and storing the position of each reactor relative to a reference reactor;

recirculating the reservoirs in the capillary reaction tube;

the central control unit can be capable of controlling the injection of drops of separating fluid between two reactors;

the central control unit can be capable of controlling the injection of at least one reagent in the reaction mixture for modifying its composition and/or its chemical and/or physical properties; and/or the central control unit can, moreover, be connected to the detector and is capable of storing at least one measurement performed by the detector or detectors.

The invention also relates to a method for monitoring a reaction in a reaction mixture, comprising the following steps:

a) filling a capillary reaction tube with a carrier medium that is immiscible with the reaction mixture;

b) injecting, by means of a capillary injection tube, an individual drop of reaction mixture in the capillary reaction tube, into the immiscible carrier fluid;

c) circulating the carrier fluid so that the drop of reaction mixture is moved relative to the capillary injection tube;

e) repeating steps b) and c) to create an ordered succession of drops of reaction mixture in the carrier fluid to form a plurality of reactors;

f) measuring at least one representative parameter of each reactor;

g) recirculating at least one reactor to measure said at least one representative parameter over time.

According to other embodiments:

the method can comprise the following steps:

a) filling a capillary culture tube with a carrier medium that is immiscible with the culture medium;

b) injecting, by means of a capillary injection tube, an individual drop of culture medium in the capillary culture tube, into the immiscible carrier fluid;

c) circulating the carrier fluid so that the drop of culture medium is moved relative to the capillary injection tube;

e) repeating steps b) and c) to create an ordered succession of drops of culture medium in the carrier fluid to form a plurality of reactors for culture of microorganisms;

f) measuring at least one parameter representative of each culture reactor, wherein said parameter can be representative of the quantity of microorganisms present in each reactor;

g) recirculating at least one reactor to measure said at least one representative parameter over time.

the method can further comprise after step c) and before step e), a step d) comprising injection, into the carrier fluid, of a drop of a so-called "separating" fluid that is immiscible with the carrier fluid and immiscible with the reaction mixture, so that at least one drop of separating fluid is interposed between two reactors and prevents their coalescence;

measurement can be performed by an optical method such as measurement of absorbance, of diffusion or of fluorescence, or by an electrical measurement such as impedance; and/or the method can further comprise, after step e), a step f) of recovery of at least one reactor of interest by aspiration of said reactor of interest into a sampling capillary tube mounted opening into the capillary reaction tube.

According to a second aspect, the invention concerns a method for monitoring reaction kinetics in a reaction medium between at least one component of the reaction medium and each of a plurality of different reagents, comprising:

generating an ordered stream of drops in a carrier fluid to form a plurality of reactors, said stream of drops comprising a series of elementary streams of drops, each elementary streams of drops being associated with at least one reagent of the plurality of reagents, each drop of an elementary stream of drops comprising the or each reagent associated with the elementary stream, circulating at least one part of the ordered stream of drops, measuring at least one parameter representative of each reagent over time.

The method according to the second aspect of the invention may comprise one or more of the following characteristics, taken alone or in all combinations technically possible:

each elementary stream comprises at least one reagent not included in an adjacent elementary stream;

generating the ordered stream of drops comprises:

generating a plurality of consecutive elementary streams of drops, each elementary streams of drops being associated with at least one reagent of the plurality of reagents, intermediate streams of drops being arranged between the elementary streams of drops, suppressing the intermediate streams of drops;

the concentration of at least one reagent varies within at least one elementary stream of drops, in particular according to a gradient;

generating the ordered stream of drops includes the following steps:

(a') generating a flow of reaction medium;

(b') filling a capillary reaction tube with a carrier fluid immiscible with the reaction medium;

(c') injecting an individual drop of reaction medium in the capillary reaction tube by means of a capillary reaction tube;

(d') circulating the carrier fluid so that the drop of reaction medium will be displaced relative to the capillary reaction tube;

(f') repeating steps c') and d') to create an ordered stream of drops of reaction medium in the carrier fluid;

the step of generating the flow of reaction medium comprises:

forming a flow of reagents comprising a series of elementary reagent flows, each elementary reagent flow comprising at least one reagent of the plurality of reagents;

mixing the reagent flow with a culture medium comprising the component to form the reaction medium flow;

forming the flow of reagents comprises the following steps:

(α) generating a continuous flow of a solvent in a mixing channel;

(β) simultaneously with step α), injecting, by means of a capillary tube, the reagent chosen from the plurality of reagents in the mixing channel to form an elementary reagent flow;

(γ) repeating step (β) for each of the successive reagents of the plurality of reagents;

forming the reagent flow comprises, after the formation of each elementary reagent flow and before step γ), a step δ) of injecting a cleaning liquid into each mixing channel by means of a capillary tube;

generating the ordered series of drops further includes, after step d) and before step f'), a step e') comprising the injection into the carrier fluid of a stop of a separating fluid immiscible with the carrier fluid or the reaction medium, such that at least one drop of separating fluid is intercalated between two reactors and prevents them coalescing;

the component is a microorganism, and the culture medium is a microorganism culture medium, and the parameter is representative of the quantity of microorganism present in each reactor;

the reagents are antibiotics, and the method comprises performing of an antibiotics resistance test to test the sensibility of the microorganism to the antibiotics.

The invention according to the second aspect also concerns a system for monitoring reaction kinetics in a reaction medium between at least one component of the reaction medium and each of a plurality of different reagents, characterized in that it comprises:

a module for the generation of an ordered stream of drops in a carrier fluid to form a plurality of reactors, said stream of drops comprising a series of elementary streams of drops, each elementary streams of drops being associated with a reagent of the plurality of reagents, whereby each drop of an elementary stream comprises the reagent associated with the elementary stream, a module for the storage and detection of the drops suitable to circulate at least part of the ordered stream of drops and to measure at least one representative parameter of each reactor over time.

The system according to the invention may comprise one or more of the following characteristics, taken alone or in any and all combinations:

the module for the generation of the ordered stream of drops includes:

means for the generation of a flow of reaction medium;

means for filling a capillary reaction tube with a carrier fluid that cannot be mixed with the reaction medium starting from a reservoir of carrier fluid;

means for the injection of an individual drop of reaction medium in the capillary reaction tube by means of a capillary reaction tube;

means for the circulation of the carrier fluid so that the drop of reaction medium will be displaced relative to the capillary reaction tube.

the means for the generation of a flow of reaction medium comprise:

means for the formation of a flow of reagents comprising a series of elementary reagent flows, each elementary reagent flow comprising at least one reagent of the plurality of reagents;

means for mixing the reagent flow with a culture medium comprising the component to form the reaction medium flow;

the means for forming the reagent flow comprise a plurality of reagent reservoirs and means for circulating each of the reagents successively starting from each of the reservoirs;

the drop storage and detection module comprises a fluid circuit for the circulation of the drops, and the means for circulation of at least part of the ordered stream of drops in the circuit by generating a pressure differential between two points on the circuit.

BRIEF DESCRIPTION OF THE DRAWINGS

Other features of the invention will be formulated in the detailed description given hereunder, referring to the appended figures which show, respectively:

FIG. 1, a schematic partial sectional view of a first functional part of the reaction system according to the first aspect of the invention;

FIG. 2, an enlarged photograph of a partial section of a capillary reaction tube according to the first aspect of the invention;

DETAILED DESCRIPTION

Figure 3:
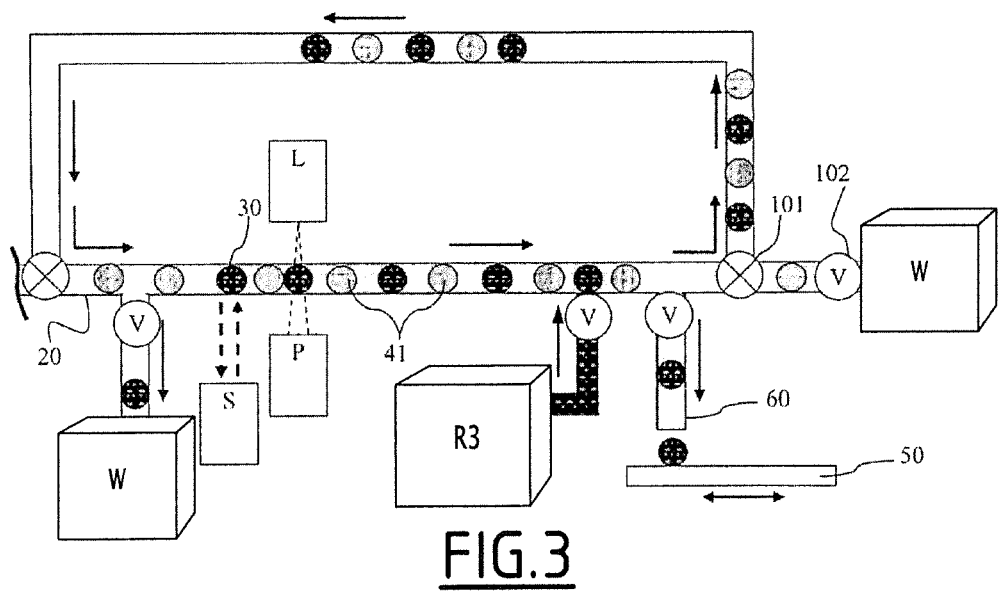
FIG. 3, a schematic partial sectional view of a second functional part of the reaction system according to the first aspect of the invention, according to a first embodiment.

In the following detailed description, the reaction system described is a system for culture of microorganisms or of living biological cells. In this application, the reaction mixture is a medium for culture of microorganisms. The other reagents can be nutrients, solutions for modifying the pH, antibiotics etc. However, the structure described can be used in other fields (chemical or experimental) for monitoring reactions over time.

In the following detailed description, a capillary tube or channel is a fluidic tube on the millimeter scale, i.e. having an inside diameter of the order of a tenth of a millimeter to a millimeter, preferably between 0.5 and 1 mm. For example, for implementing the present invention it is possible to use connectors and capillary tubes for chromatography. A preferred embodiment uses tubes with a diameter of 0.5 millimeter, making it possible to obtain drops of culture medium of about 100 nL to several milliliters.

The invention according to the first aspect proposes a method of culturing microorganisms in a culture medium comprising the following steps:
a) filling a capillary reaction tube with a carrier medium that is immiscible with the reaction mixture;
b) injecting, by means of a capillary injection tube, an individual drop of reaction mixture in the capillary reaction tube, into the immiscible carrier fluid;
c) circulating the carrier fluid so that the drop of reaction mixture is moved relative to the capillary injection tube;
e) repeating steps b) and c) to create an ordered succession of drops of reaction mixture in the carrier fluid to form a plurality of reactors;
f) measuring at least one representative parameter of each reactor or a signal resulting from the activity of said microorganisms;
g) recirculating at least one reactor in order to measure the representative parameter or parameters over time. This recirculation can be movements back and forth and/or successive passages of the succession of drops in front of the detector by the recirculating means, for measuring the quantity of microorganisms over time.

For implementing this method, the invention proposes a reaction system 100 for culture of microorganisms, a first functional part of which is illustrated in FIG. 1.

The culture reaction system 100 comprises one or more reservoir(s) M1 of culture medium 1 fluidically connected to a capillary injection tube 10. This fluidic connection is provided by T connectors.

The capillary injection tube 10 is mounted opening into a capillary culture tube 20 via a two-way valve 102.

At least one reservoir F1 of a carrier fluid 21 that is immiscible with the culture medium 1 is fluidically connected to the capillary culture tube 20 via a two-way valve 102.

The culture reaction system 100 according to the invention also comprises at least one means of circulating the culture medium 1, the carrier fluid 21 and any other fluid used in the reaction system 100 according to the invention.

This circulating means is capable of generating a flow in the various capillaries and of controlling the two-way valves 102 of the whole reaction system 100.

Advantageously, the circulating means makes it possible to generate a flow in both directions within at least certain capillaries. In other words, it is capable of reversing the direction of circulation of the carrier fluid, and therefore of the reservoirs, in some of the capillaries.

The arrangement with the capillary injection tube 10 opening into the capillary culture tube 20 makes possible the injection, by the circulating means, of individual drops 30 of culture medium 1 in the capillary culture tube 20, into the carrier fluid 21 that is immiscible with the culture medium 1. Advantageously, the injection tube is mounted opening into the culture tube via connectors, such as a T-junction or a four-way junction, equipped with one or more suitable valve(s).

The carrier fluid 21 is advantageously an oil, whereas the culture medium 1 is aqueous.

It is thus possible to produce monodispersed drops of inverted emulsion (water in oil) by controlling the flow rates (or the pressure) of the immiscible fluids. By imposing a velocity and a duration of circulation of the culture medium and/or of the carrier fluid, it is possible to accurately inject a defined volume of culture medium into the carrier fluid in the form of individual drops.

Each drop 30 constitutes a reactor for culture of microorganisms within the carrier fluid 21.

The reaction system for cultures of microorganisms according to the invention advantageously comprises one or more reservoirs R1, R2 of reagent 51, 52 fluidically connected to the capillary injection tube 10 via T-connectors (see FIG. 1) and/or to the capillary culture tube 20 (see reservoir R3 in FIG. 3 directly connected to the culture tube 20), so that reagent 51, 52 can be mixed with the culture medium 1. This makes it possible to modify the composition and/or the chemical and/or physical properties of the culture medium, then referenced 1'. For example, it is possible to enrich or deplete a reactor 30 of nutrients, modify the pH, inject labeling molecules, for example fluorescent, inject molecules whose stimulating or inhibitory capacity is to be tested on the microorganisms (for example antibiotics), etc.

It is thus possible to define the composition of the culture medium precisely by adjusting the flow rates of the fluids constituting the aqueous phase.

To prevent the risks of coalescence and difficulties with detection connected with the closeness of the reservoirs 30, the invention advantageously proposes interposing another fluid that is immiscible with the culture medium 1, 1' and with the carrier fluid 21.

Thus, after step c) and before step e), the invention envisages a step d) comprising injection, in the carrier fluid 21, of a drop of a so-called "separating" fluid, immiscible with the carrier fluid and immiscible with the culture medium, so that at least one drop 40 of separating fluid is interposed between two culture reactors 30 and prevents their coalescence.

For this purpose, the reaction system of cultures of microorganisms according to the invention advantageously comprises at least one reservoir F2 of a separating fluid 41 that is immiscible with the carrier fluid 21 and immiscible with the culture medium 1, 1'.

This reservoir F2 is fluidically connected to the capillary culture tube 20 via a two-way valve 102 so that drops 40 of separating fluid can be injected into the carrier fluid 21 between two culture reactors 30.

The carrier fluid 21 and the separating fluid 41 are preferably mutually immiscible oils, for example fluorinated oil as carrier fluid and mineral oil for the separating fluid, the culture medium 1,1' being an aqueous medium that is immiscible with the aforementioned oils 21, 41.

The length of the capillary culture tube in which the reactors are formed, and the flow rates imposed, define the quantity of reactors that can be used per experiment and the time interval between each measurement. It is thus possible to work on several thousand reactors in parallel. This method of manipulating drops in one dimension makes it possible to preserve the identity of each drop in the course of an experiment, and control their composition perfectly by avoiding any loss by evaporation or transfer.

According to a preferred embodiment, the method according to the invention comprises, after step e), a step f) of measuring one or more representative parameters of each culture reactor 30, wherein said parameter can be representative, for example, of the quantity of microorganisms present in each reactor.

Measurement can be performed by an optical method such as measurements of absorbance, of diffusion or of fluorescence, or by an electrical measurement such as impedance.

A first embodiment of a second functional part of the reaction system according to the invention is illustrated in FIG. 3. This second functional part makes it possible to carry out the aforementioned steps of the method.

For this purpose, capillary culture tube 20, at least, comprises at least one portion that is transparent to a signal emitted and/or captured by a detector S, or a detector L-P.

Detector S can be an electrical impedance sensor.

Detector L-P consists, in this example, of a laser L emitting optical excitation radiation, and a photodiode P sensitive to the radiation emitted by the reservoir 30 under excitation of the laser, which can be positioned on the axis or at an angle to the excitation radiation (in the case of dispersion of light, the light dispersed by the drop at 90° of the laser or any other angle can be observed).

The embodiment illustrated in FIG. 3 comprises a means for recirculating the reservoirs comprising a loop for recirculating the reactors in front of the detector or detectors S, L-P. This recirculating loop then comprises a capillary discharging upstream and downstream of the detector or detectors S, L-P. In this case the circulating means for the fluids (culture medium, carrier fluid) can function only in a single direction of circulation.

It is thus possible to monitor the growth of the microorganisms in each reservoir by mechanically displacing the carrier fluid, thus making each reactor pass repeatedly (recirculation of the reactors) in front of the detector or detectors S or L-P, in the same direction of circulation. This displacement is very easy to implement, and does not risk overturning the reactors, as with the plates of the prior art. Thus, the speed of displacement can be accelerated, the more so if there are drops of separating fluid 40 between each reactor 30.

Figure 4:
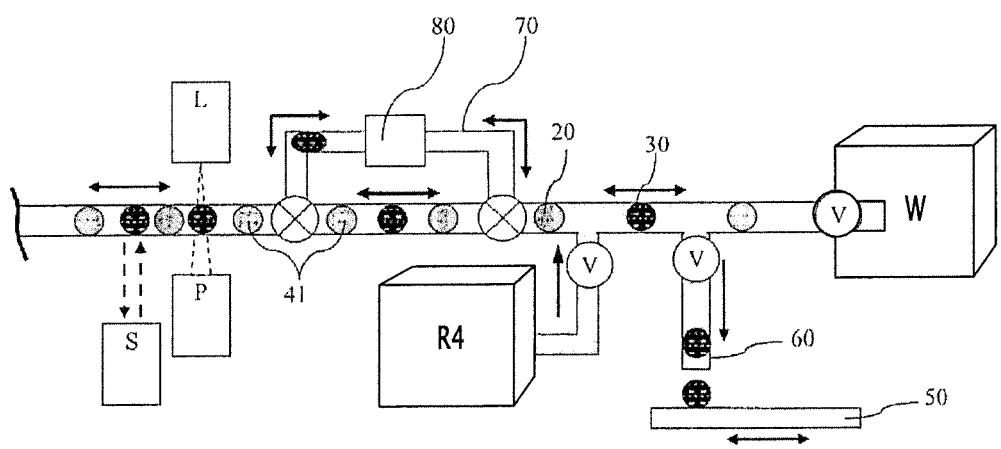
FIG. 4, a schematic partial sectional view of a second functional part of the reaction system according to the first aspect of the invention, according to a second embodiment.
Figure 5:
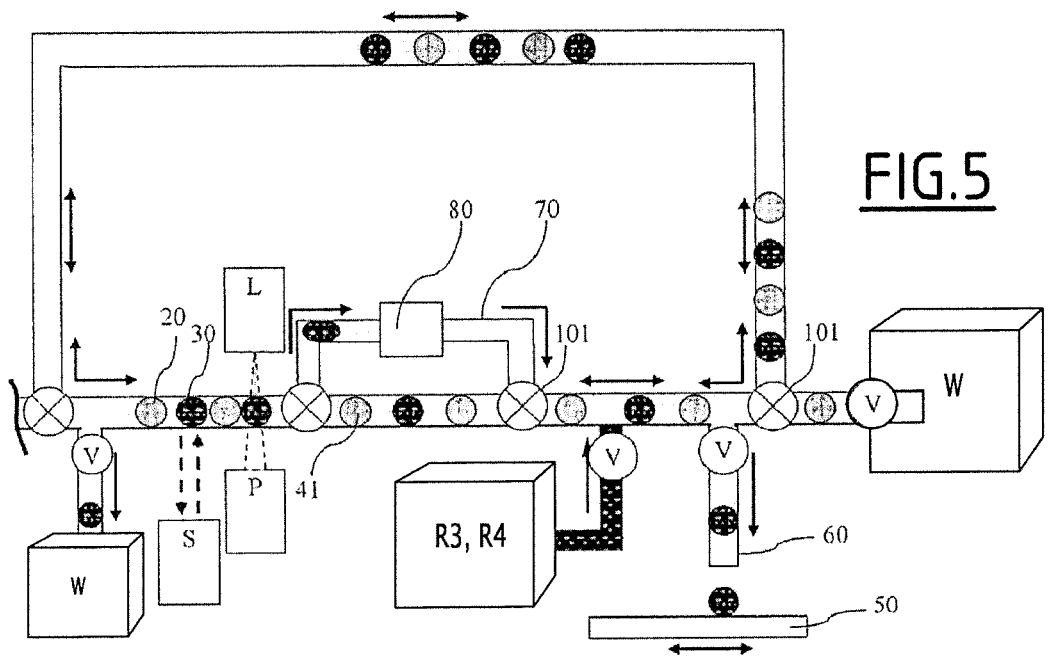
FIG. 5, a schematic partial sectional view of a second functional part of the reaction system according to the first aspect of the invention, according to a third embodiment.

Alternatively, as illustrated in FIG. 4, or in combination, as illustrated in FIG. 5, the means for circulating the fluids can function bidirectionally, i.e. leading the fluids through the capillaries in one direction or in the opposite direction.

It is thus possible to monitor the growth of the microorganisms in each reservoir by mechanically displacing the carrier fluid back and forth, to recirculate each reactor in front of the detector or detectors S or L-P.

By combining a recirculating loop and a means for circulating the fluids functioning bidirectionally (FIG. 5), it is possible to reduce the time between two passages of one and the same reactor in front of the detector or detectors, optimizing the recirculation as a function of the distances upstream and downstream of the reservoir relative to the detectors. Thus, depending on the user's requirements and on the particular case, it will be advantageous to reverse the direction of circulation of the fluid to bring a reactor of interest in front of the detector or detectors S or L-P, or, conversely, to continue circulating the carrier fluid in the same direction, to recirculate the reactor of interest via the recirculating loop.

Figure 6:
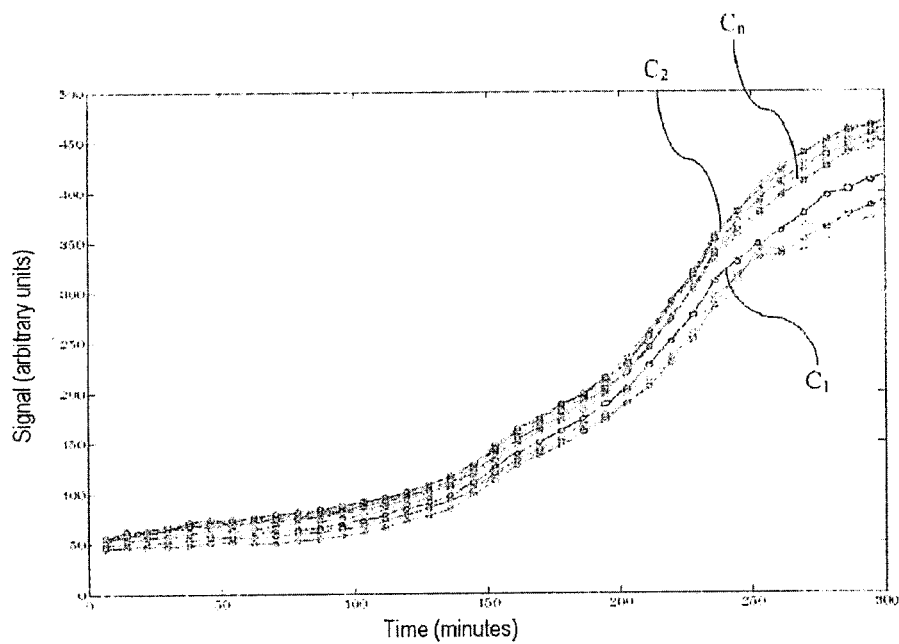
FIG. 6, an example of curves of measurements for monitoring the growth of populations of microorganisms in a reaction system according to the first aspect of the invention.

Knowing the position of each reactor in the succession of reactors precisely, and knowing the chemical and/or physical characteristics of the culture medium, it is possible to analyze the influence of the composition of the culture medium on the growth of the microorganisms. Measurement curves C1, C2, Cn of the population of microorganisms in a plurality of reactors are shown in FIG. 6.

It is thus possible to measure the variation of the population of microorganisms in each successive reservoir over time by performing successive passages of the reservoirs, in the same direction of circulation (FIGS. 3 and 5) and/or by alternating the direction of circulation (FIGS. 4 and 5), in front of the detectors. Each curve represents an identified reactor and each point represents the passage of the reactor in question in front of the detector at a given time interval. Thus, each drop is identified, measured and parameterized.

A reservoir R4 of carrier fluid can be mounted opening into the culture capillary 20 for separating the drops before sorting them (FIG. 4). This reservoir R4 can of course be provided in combination with one or more reservoirs R3 of reagents such as that illustrated in FIGS. 3 and 5.

As illustrated in FIGS. 3 to 5, the microorganism culture sorter according to the invention preferably comprises at least one waste reservoir W, connected fluidically to the capillary culture tube 20 for removing the reactors after the experiment and valves 101-102 for orienting the drops.

The invention also permits easy selection and extraction of a culture reactor of interest. Thus, the invention proposes, after step e), a step f') of recovery of at least one culture reactor of interest by aspiration of said reactor of interest into a sampling capillary tube 60 mounted opening into the capillary culture tube 20.

Advantageously, the sampling capillary tube allows the sampled reactor to be deposited on a culture substrate 65, such as a layer of agar or in the wells of a microplate.

Thus, during detection, each reactor is tagged with its position in the succession, and a counting detector allows the reservoirs to be identified. By means of valves 102, the reactor or reactors of interest are directed into the sampling capillary tube 60, whereas the other reactors remain in the capillary culture tube 20. The reactor or reactors of interest are recovered at the outlet of the sampling capillary tube 60.

The reverse is also possible: the reactors of interest are kept in the capillary culture tube 20, while the other reactors are collected and removed. Then only the reactors of interest for the experiment remain in the culture tube 20.

Alternatively, or in combination, the invention advantageously envisages at least one diverting capillary tube 70 mounted opening into the capillary culture tube 20 so that at least one culture reactor 30 can be diverted to a treatment means 80 of one or more reactors 30. This treatment means 80 can be a thermal regulating means that can heat or cool one or more reactors. Other treatment means can be provided such as the addition of culture medium or sampling of a portion of the reactor for making a chemostat (bioreactor in which organisms (bacteria, phytoplankton) grow in a controlled manner).

The diverting capillary tube 70 thus permits selective treatment of one or more reactors relative to the other reactors that remain in the culture tube 20. It will be understood that several diverting tubes can be provided so that reactors 30 diverted selectively can be treated differently.

The invention is advantageously implemented by means of a central control unit connected to the circulating means and capable of:
- controlling the injection of individual drops of culture medium in the capillary culture tube, into the carrier fluid, imposing a velocity and a duration of circulation of the culture medium, so as to form a plurality of reactors 30 for culture of microorganisms;
- controlling the circulation of the carrier fluid by imposing a velocity, duration and direction of circulation of the carrier fluid in the capillary culture tube by controlling the valves;
- counting the culture reactors 30 in the carrier medium and storing the position of each reactor relative to a reference reactor 30;
- recirculating the reservoirs 30 in the capillary reaction tube;
- controlling the injection of drops 41 of separating fluid between two culture reactors 30;
- controlling the injection of at least one reagent 51, 52 into the culture medium 1, 1' for modifying its composition and/or its chemical and/or physical properties;
- controlling the sampling of at least one reactor of interest; and/or
- controlling the diverting of at least one reactor of interest to a treatment means, itself advantageously controlled by the central unit.

Advantageously, the central control unit is, in addition, connected to the detector S, L-P and is capable of storing at least one measurement performed by the detector.

Advantageously, the reaction system comprises a thermal regulating means of the reactors which is preferably arranged to allow thermal regulation in the whole reaction system. This thermal regulation can be homogeneous, i.e. roughly identical throughout the system, or heterogeneous, i.e. the temperature can be increased in certain places and decreased in other places of the system.

However, this method is limited to the study of a single reagent or a single mixture of reagents, such that the degree of automation of this method is limited. This invention seeks to address the aforementioned disadvantages and to provide an automatic reaction monitoring method that allows for the simultaneous variation of the type of reagent analysed and its concentration during a single experiment, and allows for monitoring of the reaction kinetics.

Figure 7:
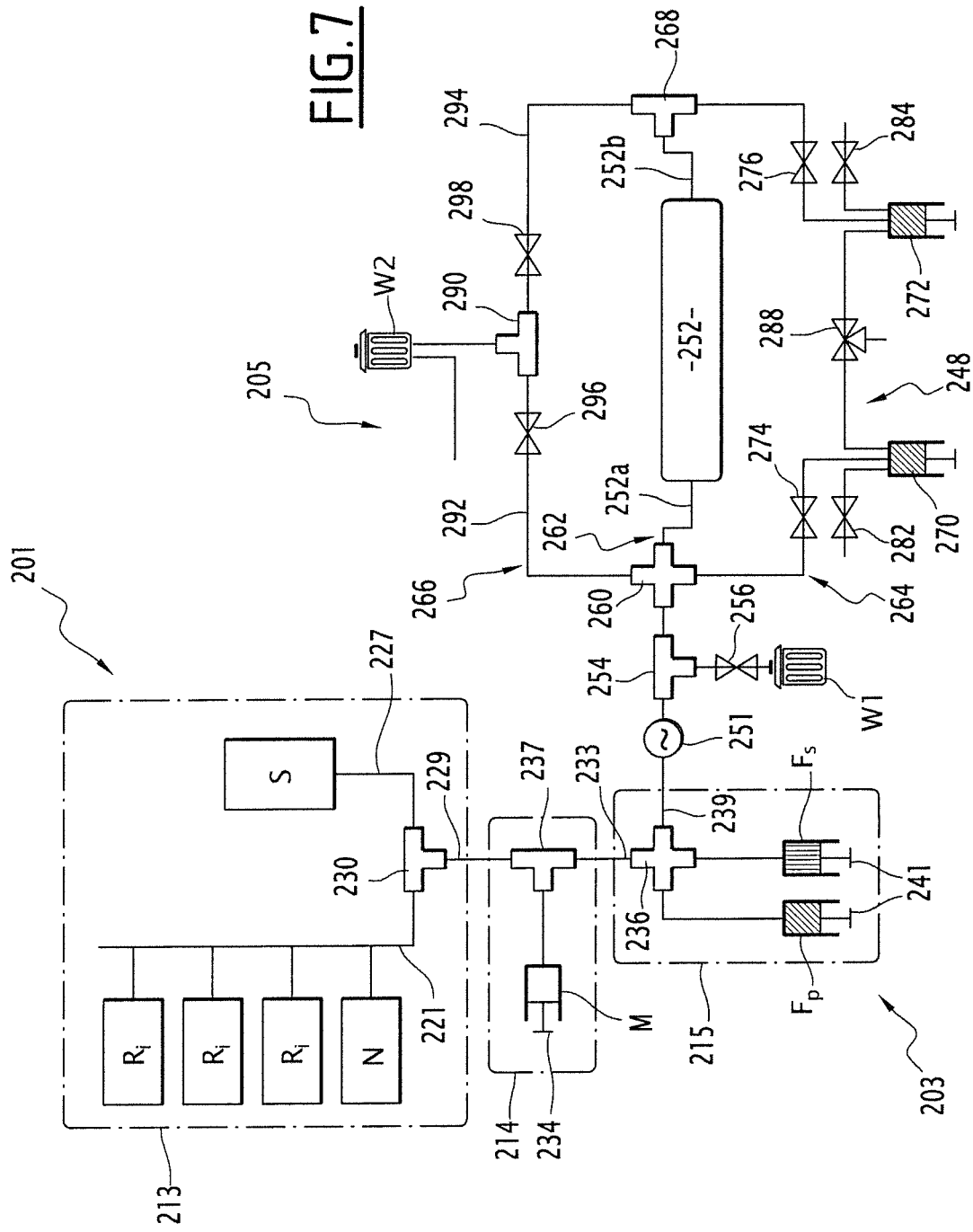
FIG. 7 is a schematic representation of a reaction system according to the second aspect of the invention.
Figure 9:
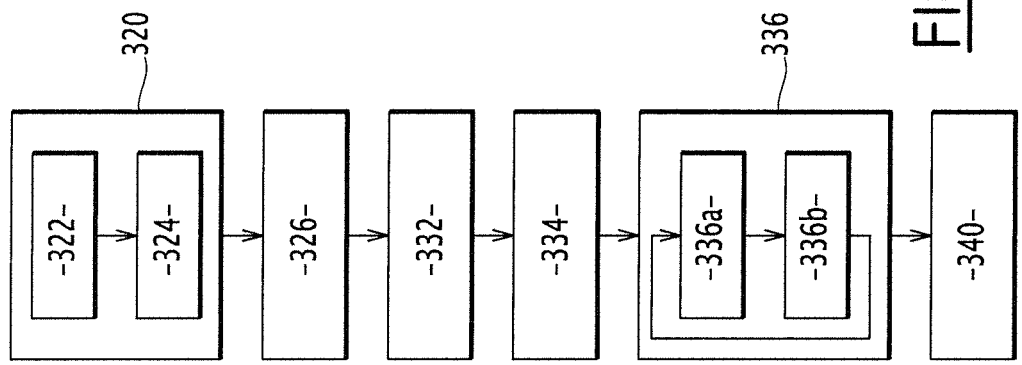
FIG. 9 is a schematic summarizing the steps of a method according to the second aspect of the invention.
Figure 8:
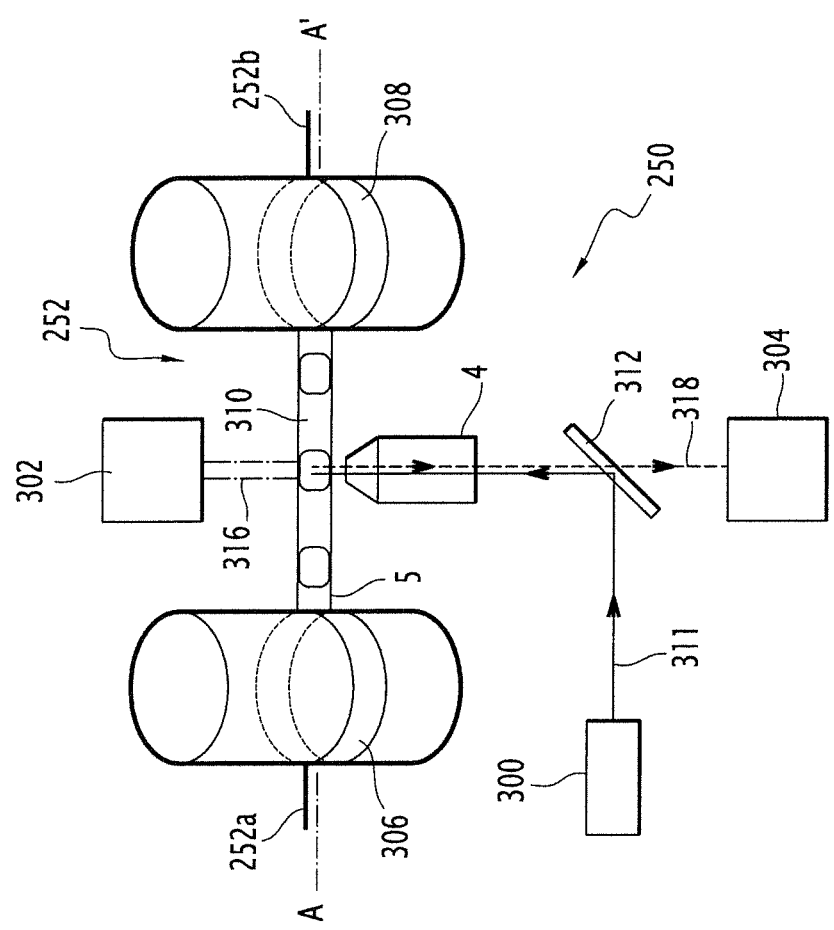
FIG. 8 is a schematic detail view of the system of FIG. 7.

The second aspect of the invention will now be described with reference to FIG. 7-9.

The system 201 according to the second aspect of the invention includes a module 203 for generating a stream of drops, a module 205 for storing and detecting the drops formed by the module 203, and a module for controlling the modules 203 and 205.

The module 203 for generating a stream of drops is suitable to generate an ordered stream of drops of reaction medium in a carrier fluid in a capillary reaction tube. This ordered stream consists of a series of elementary streams, each of which is associated with at least one given reagent Each drop of an elementary stream thus includes, in addition to a culture medium, the one or more reagents $r_i$ associated with the elementary stream $t_i$ at a given concentration.

Additionally, to avoid the risk of coalescence of the drops, a separating fluid that is not miscible with the carrier fluid or the reaction medium is intercalated between two drops of the stream of drops.

Two adjacent elementary streams differ from one another in that at least one of the elementary streams comprises at least one reagent that is absent from the other elementary stream.

As described below, each elementary stream consists of drops in which the concentration of at least one reagent is variable. Each elementary stream comprises either a single reagent, the concentration of which is variable within the elementary stream, or a combination of several reagents, the concentration of at least one of which is variable within the elementary stream.

Preferably, the concentration of the reagent in the elementary stream of drops forms a gradient between a minimum concentration, e.g., nil, and a maximum concentration. The concentration of the reagent $r_i$ thus varies uniformly within the stream between these two concentrations.

For example, an elementary stream may comprise a first reagent $r_i$, the concentration of which is constant within the stream of drops, and a second reagent $r'_i$, the concentration of which varies within the elementary stream, in particular according to a gradient.

According to another example, an elementary stream may comprise a first and second reagent $r_i$ and $r'_i$, whereby the concentration of each of the reagents $r_i$ and $r'_i$ varies within the elementary stream according to a gradient, chosen, e.g., such that the ratio between the concentrations of these reagents is substantially constant within the stream of drops.

To generate this stream of drops, the module 203 includes a unit 213 for generating multiple gradients, a unit 214 for generating a flow of reaction medium, and a unit 215 for generating the stream of drops.

The gradient generation unit 213 is suitable to generate a liquid flow consisting of a series of elementary flows, each of which consists of at least one reagent diluted in a solvent, within a capillary reaction tube.

Advantageously, the concentration of at least one reagent in the solvent varies within each elementary flow, preferably uniformly, in particular in a linear fashion.

Additionally, two consecutive elementary flows are advantageously separated by an intermediate flow in order to avoid contamination of one elementary flow by a reagent from the previous elementary flow. This intermediate flow comprises, e.g., the solvent and a cleaning liquid, as well as traces of the one or more reagents of the previous elementary flow.

The unit 213 includes a plurality of reagent reservoirs $R_i$, each comprising a different reagent $r_i$, fluidically connected with a capillary reagent injection tube 221 via a T connector, as well as a cleaning liquid n reservoir N, also fluidically connected with the capillary reagent injection tube 221 via a T connector.

The unit 213 further includes a solvent s reservoir S, fluidically connected with a capillary solvent injection tube 227.

The capillary reagent injection tubes 221 and the solvent 227 are mounted opening into a mixing channel 229 via a T connector 230.

The unit 213 additionally includes means for circulation of the reagents $r_i$, the solvent s, and the cleaning liquid n.

These circulation means are suitable to generate a flow rate of each of the reagents $r_i$ and the cleaning liquid n in the capillar reagent injection tube 221 from each of the reagent reservoirs $R_i$ and from the cleaning liquid reservoir N to the mixing channel 229. These circulation means are also suitable to generate a flow rate of solvent s in the capillary solvent injection tube 227 from the solvent reservoir S to the mixing channel 229.

In particular, to generate a plurality of elementary flows, each of which consists of various reagents diluted in a solvent, the circulation means are suited to generate a continuous flow of solvent in the tube 227, and, simultaneously, to sequentially generate a flow of each of the groups of reagents in the tube 221, whereby a cleaning liquid flow is generated in the tube 227 between two consecutive flows of reagents.

These circulation means comprise, e.g., a HPLC-type sampler (for high-performance liquid chromatography). In one variant, the reservoirs Ri and S are wells of a plate, and the circulation means comprise an automatic device capable of pipetting the reagents $r_i$ or the solvent s from the wells.

In another variant, the reservoirs Ri and S are connected to a pressure generator via a pressure multiplexer. The pressure multiplexer comprises valves that may be opened or closed, the opening of which generates the injection of a selected reagent under a pressure emanating from the pressure generator to the capillary reagent injection tube 221.

The mixing channel 229 comprises two liquid inputs, respectively connected to the tube 221 and the tube 227, such that each reagent $r_i$ or the cleaning liquid n is mixed with the solvent in the mixing channel 229 by means of Taylor-Aris diffusion.

Thus, the mixing channel 229 is suited to provide a liquid flow, referred to as the reagent flow, at its output. This reagent flow consists of a series of elementary reagent flows, whereby two consecutive elementary reagent flows are separated by an intermediate flow consisting of solvent and cleaning liquid, as well as traces of the reagents $r_i$ of the previous elementary flow.

For example, the mixing channel 229 and the circulation means are configured such that, in each, or at least some, of these elementary flows, the concentration of at least one reagent $r_i$ varies linearly between a minimum and a maximum concentration.

The injection of cleaning liquid allows for rinsing of the capillary reagent injection tube 221 and the mixing channel 229 between two consecutive reagent injections, thus avoiding contamination by a reagent of a given elementary flow of the following elementary flow if the presence of this reagent is not desired in the following elementary flow.

In particular, due to the injection of the cleaning liquid, each elementary flow comprises at least one reagent absent from the previous or subsequent elementary flow.

The reaction medium flow generation unit 214 is suited to generate a flow of reaction medium in a capillary reaction medium injection tube 233, by mixing the consecutive elementary flows emanating from the unit 213 and a culture medium flow.

The unit 214 thus includes a culture medium m reservoir M, fluidically connected with the outlet of the mixing channel 229 by means of a T connector 237, such that the culture medium m may be mixed successively with each of the elementary reagent flows in a capillary injection tube 233. The mixture thus obtained, having a variable composition, is referred to as the reaction medium.

The culture medium m comprises microorganisms such as cells or bacteria.

The unit 214 further includes circulation means 234 for the culture medium m suited to control the flow rate of the culture medium m towards the T connector 237 relative to the flow rate of the liquid emanating from the unit 213, so as to obtain a reaction medium of the desired composition in the tube 233, in particular to control the final concentration of reagents in the reaction medium.

The drop stream generation unit 215 is suited to generate a stream of drops in a capillary reaction tube 239, in particular from the reaction medium flow emanating from the unit 214, a carrier fluid flow $f_p$, and from a separating fluid $f_s$ flow.

The unit 215 thus includes a reservoir Fp for carrier fluid $f_p$ and a reservoir Fs for separating fluid $f_s$.

The separating fluid $f_s$ is a fluid that is not miscible with the carrier fluid $f_p$ or with the culture medium m. The carrier fluid $f_p$ and the separating fluid $f_s$ are preferably mutually non-miscible oils, e.g., fluorinated oil as the carrier fluid and mineral oil as the separating fluid, whereby the culture medium m is an aqueous medium that is not miscible with the aforementioned oils.

The reservoirs Fp, Fs for the carrier fluid $f_p$ and the separating fluid $f_s$ and the capillary injection tube 233 are mounted so as to open into the capillary reaction tube 239 via a cross junction 236 having suitable butterfly valves.

The unit 215 additionally includes means 241 for circulation of the carrier fluid reagents $f_p$, and the separating fluid $f_s$.

These circulation means 241 are suited to control the flow rate of the carrier fluid $f_p$ and the separating fluid $f_s$ out of the reservoirs Fp, Fs for the carrier fluid $f_p$ and the separating fluid $f_s$ towards the tube 239.

For example, the reservoirs Fp, Fs for the carrier fluid $f_p$ and the separating fluid $f_s$ comprise syringes, and the circulation means 241 comprise syringe pumps. In one variant, the circulation means 241 are suitable to apply a controlled pressure of the reservoirs Fp, Fs to generate a fluid flow from these reservoirs.

The control of the respective flow rates of the reaction medium, carrier fluid, and separating fluid allows for the formation of monodispersed inverse emulsion drops (water in oil). By setting a speed and circulation time for the reaction medium, carrier fluid, and separating fluid, a determined volume of reaction medium, and, alternatively, of separating fluid may be injected precisely into the carrier fluid in the form of individual drops.

Each drop of reaction medium thus formed consists of a microorganism culture reactor in the carrier fluid $f_p$.

The drop stream generation unit 215 thus allows for the formation of a stream of drops of reaction medium in the carrier fluid, in which two consecutive drops of reaction medium are advantageously separated by a drop of separating fluid. Due to the composition of the reaction medium formed by the unit 214, the stream of drops includes a series of elementary streams of drops, each of which is associated with at least one of the reagents $r_i$, whereby two consecutive elementary streams are separated by an intermediate stream of drops consisting of solvent and cleaning liquid but none of the reagent $r_i$, except in the form of traces.

Additionally, in each elementary stream of drops, the concentration of at least one reagent $r_i$ varies from one drop to the next according to a gradient, e.g., in a linear fashion.

The length of the capillary reaction tube 239, in which the drops are formed, and the flow rates determined define the quantity of drops that may be used per experiment and the time between each measurement. Thus, it is possible to work on several thousand drops simultaneously. This method for manipulating drops at one dimension allows for the maintenance of the identity of each drop over an experiment and for perfect control of their composition, avoiding any loss due to evaporation or spillage.

The storage and detection module 205 for the drops of reaction medium comprises a circuit 248 for circulating the drops and a storage and detection unit 250 for the drops.

The circuit 248 is insulated from the module 203 for generating a stream of drops by a pinch valve 251.

The capillary reaction tube 239 opens into the circuit 248 at a T connector 254, followed by a two-way valve 256, allowing the stream of drops to be orientated either towards the storage and detection unit 250 or a waste reservoir W1.

In particular, such an arrangement allows for the elimination of drops containing cleaning liquid, i.e., the drops of the intermediate streams, from the stream of drops. The stream of drops received by the unit 250 thus consists of a series of elementary streams of drops of reaction medium, each comprising at least one reagent. Furthermore, each elementary stream comprises at least one reagent not included in an adjacent elementary stream.

The T connector 254 opens into the circuit 248 at a cross junction 260 that is further connected with three branches 262, 264, 266 of the circuit 248.

A first branch 262 opens into a channel 252 of the storage unit 250. As described in greater detail by reference to FIG. 8, the storage unit 250 comprises a linear detection channel 252, extending between two ends, referred to below as 'inlet' 252a and 'outlet' 252b, between which the fluid may flow in two opposite directions of circulation. The inlet 252a of the detection channel 252 is fluidically connected to the cross junction 260, whilst the outlet 252b is fluidically connected to a T connector 268.

The two other branches 264, 266 also extend between the cross junction 260 and the T connector 268.

These two branches 264, 266 comprise means for circulating the stream of drops allowing for the generation of displacements of the stream of drops in the linear detection channel 252 in both directions of circulation, thus permitting multiple measurements over time for each drop of the stream.

In particular, the branch 264 comprises means for generating a positive or negative pressure differential between the inlet 252a and the outlet 252b of the detection channel 252, thus causing a displacement of the stream of drops contained in the channel 252 in one or the other direction.

To this end, the branch 264 includes two reservoirs 270, 272 for the carrier fluid $f_p$, fluidically connected respectively to the cross junction 260 and the T connector 268 by means of two-way valves 274, 276.

First pressurisation means are suitable to apply a pressure $P_0$ to each of the reservoirs 270, 272, via valves 282, 284. Thus, when the valve 282 (or 284) is open, the carrier fluid $f_p$ contained in the reservoir 270 (or 272) is kept at the pressure $P_0$ by the first pressurisation means.

Second pressurisation means 286 are suitable to selectively apply a pressure P, greater than $P_0$, to one or the other of the reservoirs 270 or 272, via a valve 288.

The application of the pressure P on the reservoir 270 (or 272) is suited to generate a flow of carrier fluid $f_p$ from this reservoir towards the detection channel 252 via the cross junction 260 (or the T connector 268), i.e., a displacement of the stream of drops in this channel 252 from the inlet 252a (or outlet 252b) towards the outlet 252b (or inlet 252a).

The branch 266 comprises liquid evacuation means exiting the channel 252 towards a waste reservoir W2.

To this end, the branch 266 includes a waste reservoir W2, connected, via a T connector 290, on the one hand to an upstream capillary culture tube 292 opening into the cross junction 260, and on the other to a downstream capillary culture tube 294 opening into the T connector 268.

The upstream 292 and downstream 294 capillaries each have a two-way valve 296 or 298.

Each valve 296 or 298, when closed, allows a liquid flow to be stopped in the upstream 292 or downstream 294 capillary. In particular, the valves 296, 298 allow a flow of carrier liquid $f_p$ from the reservoir 270 or 272 to be guided towards the detection channel 252, whilst preventing the movement of this flow into the waste reservoir W2, and guiding a liquid flow from the detection channel 252 towards the reservoir 270 or 272, or preventing the movement of this flow towards the waste reservoir W2.

Conversely, when the valve 296 or 298 is closed, it allows a liquid flow into the upstream 292 or downstream 294 capillary culture tube. In particular, the valve 296 or 298 allows a liquid flow from the channel 252 towards the waste reservoir W2 during the movement of the stream of drops in the channel 252.

The branch 266 allows, in particular, for the emptying and rinsing of the detection circuit 48 after the completion of measurements by injecting carrier fluid into the channel 252 via one of the reservoirs 270 or 272 and the evacuation of the content of this channel 252 via the upstream 292 or downstream 294 capillary culture tube into the waste reservoir W2.

The storage and detection unit 250 will now be described in greater detail by reference to FIG. 8.

The storage and detection unit 250 comprises means for referencing the drops in order to identify them in the stream of drops, and means for monitoring the reactions occurring in each of the drops.

To this end, the storage and detection unit 250 comprises the linear detection channel 250, and drop detection and counting means comprising a light source 300 and at least one detector 302, 304.

The detection channel 252 consists, for example, of a capillary culture tube comprising two portions, upstream 306, and downstream 308, coiled on two spools, and a capillary measurement section 310 arranged between the upstream 306 and downstream 308 portions. The capillary measurement section 310 defines a central axis A-A'.

The upstream 306 and downstream 308 portions, coiled on two spools, allow for storage of the stream of drops whilst minimising the space necessary for storage. The two portions, upstream 306 and downstream 308, are fluidically connected respectively to the inlet 252a and the outlet 252b of the channel 252.

The lengths of the upstream 306 and downstream 308 portions are selected to be greater than the length of the stream of drops analysed, such that all drops of the stream may pass into the capillary measurement section 310 without any drop leaving the channel 252.

Advantageously, the upstream 306 and downstream 308 portions are arranged in a temperature-controlled enclosure in which the gas concentrations and the lighting are controlled.

The wall of the capillary measurement section 310 is at least partially transparent to the light radiation emitted by the light source 300 and the light captured by the one or more detectors 302, 304.

The light source 300 is arranged transversely on one side of the central axis A-A'. It preferably includes a laser.

The source 300 is suited to emit a coherent incident beam 311 directed towards the capillary measurement section 310 after reflecting off of at least one mirror 312 and after being focused by a lens 314.

Advantageously, the incident beam 311 is a laser beam having a wavelength between 400 and 800 nm.

Preferably, the mirror 312 is a dichroic mirror suited to reflect the light rays emitted by the source 300 and to transmit light rays having a wavelength in a predetermined range, e.g., between 400 and 800 nm.

A first detector 302, arranged on another side of the central axis A-A', is suitable to receive an output beam 316 arising from the incident beam passing through the capillary measuring section 310.

The angle of incidence of the incident beam 311 on the capillary measurement section 310 is, e.g., equal to 0°. The first detector is this suited to determine, based on the output beam 316, the optical density of the fluid passing through the capillary measurement section 310, and thus of each of the drops of the stream of drops. The determination of the optical density allows for a determination of the content of each drop, in particular its biomass. In particular, in the context of multiple antibiotics resistance tests, it is thus possible to measure the bacterial concentration of a drop each time a given drop passes through the capillary measurement beam.

The detector 302 may also be arranged at an angle of up to 90° relative to the incident beam 311 to measure the light diffused by each drop.

Advantageously, the reaction medium forming each drop is loaded with an optically active, e.g., fluorescent, product. Thus, each drop receiving the incident beam 311 can emit a reflected beam 318 having a wavelength advantageously between 400 and 800 nm. This reflected beam 318 is this suited to be transmitted via the mirror 312.

A second detector 304, arranged opposite the mirror 312 on the same side of the central axis A-A', is suitable to receive the reflected beam 318, and thus to detect the passage of each drop through the capillary measuring section 310.

The detectors 302 and 304 comprise, e.g., an LED or a photon multiplier tube.

The storage and detection unit 250 thus allows for simultaneous detection and referencing of every drop during its multiple passages through the channel 252 and monitoring of the reactions taking place in each drop over time.

The control module is suited to control the modules 203 and 205, in particular the circulation means of the various fluids, in particular the valves and syringes, and to receive and process the information obtained from the detectors 302 and 304 in order to reconstruct the measurement results.

A reaction monitoring method according to an embodiment of the invention, implemented by means of the monitoring system, will now be described by reference to FIG. 9.

This method comprises the generation by the module 203 of an ordered stream of drops of reaction medium in the carrier fluid $f_p$, in the capillary reaction tube 239.

To this end, in a step 320, the module 203 generates a flow of reaction medium in the capillary injection tube 233.

This stage 320 includes a step 322 in which the unit 213 generates a reagent flow consisting of a series of reagent gradients in the capillary injection tube.

In this phase 322, the circulation means 231 successively generate a flow of each of the reagents $r_i$ from each of the reservoirs $R_i$ in the capillary reagent injection tube 221 towards the mixing channel 229, whilst intercalating a flow of cleaning liquid n from the reservoir N in the tube 221 towards the mixing channel 29 after each flow of a reagent $r_i$.

Simultaneously, the circulation means 232 generate a flow of solvent s in the capillary solvent injection tube 227 from the solvent reservoir S to the mixing channel 229.

The flow of reagents $r_i$ and the cleaning liquid n successively arrive at the mixing channel 229 in which they are mixed with the solvent s and undergo a Taylor-Aris diffusion.

Thus, the mixing channel 229 provides, at its outlet, a liquid reagent flow consisting of a series of gradients of reagents $r_i$ between which the liquid flows consisting of a mixture of solvent and cleaning liquid, without any of the reagents $r_i$, are intercalated.

For example, the concentration of each of the reagents $r_i$ varies in a linear fashion within a gradient between a minimum and maximum concentration.

In the phase 322, the relative flow rates of the various reagents relative to the solvent flow may be adjusted independently of one another so as to obtain a precise adjustment of the minimum and maximum concentration of each of the reagents $r_i$ in each drop of the associated elementary stream.

The phase 322 is followed by a phase 324 in which the unit 214 generates a flow of reaction medium in the capillary injection tube 233 by mixing the reagent flow with a culture medium flow m from the reservoir M.

In this phase 324, the circulation means 234 generate a flow of culture medium m via the T connector 237 in the capillary injection tube 233, in which the flow of culture medium m is mixed with the reagent flow, thus mixing successively with each of the reagent gradients.

Then, in a step 326, the unit 215 generates a stream of drops from a flow of reaction medium from the capillary injection tube 233, a flow of carrier fluid $f_p$ and a flow of separating fluid $f_s$.

In this step 326, the circulation means 241 generate a flow of carrier fluid $f_p$ towards the capillary reaction tube 239 and cause an injection of individual drops of reaction medium from the capillary injection tube 233 in the capillary reaction tube 239 in the carrier fluid $f_p$, which is not miscible with the reaction medium.

Additionally, after each injection of a drop of reaction medium, the circulation means 241 cause an injection of at least one individual drop of separating fluid $f_s$ in the capillary reaction tube 239 in the carrier fluid $f_p$. Thus, at least one drop of separating fluid is intercalated between two drops of reaction medium, preventing their coalescence.

Thus, in the step 326, a stream of drops of reaction medium is formed in the capillary reaction tube 239, consisting of a series of elementary streams, each of which is associated with a reagent $r_i$, whereby each elementary stream consists of a series of drops including the reagent $r_i$ at a given concentration.

In each elementary stream of drops, the concentration of reagent $r_i$ varies from one drop to the next according to a gradient, e.g., in a linear fashion.

Two consecutive drops of reaction medium are separated by a drop of separating fluid $f_p$. Additionally, two consecutive elementary streams are separated in the capillary reaction tube 239 by an intermediate stream comprising various drops formed by mixing culture medium m, solvent s, and cleaning liquid n, as well as traces of the one or more reagents of the previous elementary stream.

Then, in a sorting step 332, the stream of drops is transferred from the drop stream generation module 203 to the drop circulation circuit 248 via the pinch valve 251 and the T connector 254. When passing through the junction 254, the drops are sorted either towards the waste reservoir W1 or the drop circulation circuit and detection 248 depending on their content, which is determined based on the position of the drops in the stream.

In particular, when drops of an elementary stream of drops arrive at the junction 254, the valve 256 is closed, such that the drops are orientated towards the drop circulation circuit 248. On the other hand, when drops of an intermediate stream of drops arrive at the junction 254, the valve 256 is opened, such that the drops are orientated towards the waste reservoir W1 for disposal.

The stream of drops received by the storage unit 250 thus consists of a series of elementary streams of drops of reaction medium, each comprising at least one reagent.

In a step 334, the stream of drops is transferred to the channel 252. To this end, the valves 274, 276, and 296 are closed, and the valve 298 is open, which requires the stream of drops to pass through the cross junction 260 to the detection channel 252. The entirety of the drop circulation circuit 248 is preferably initially loaded with carrier fluid. Thus, in step 334, the carrier fluid initially contained in the channel 252 is pushed by the stream of drops through the junction 268, the valve 298, and the junction 290 to the waste reservoir W2.

Once the entire stream of drops is transferred to the detection channel 252, the stream of drops is subjected, in a measuring step 336, to a back-and-forth movement in the channel 252 such that each drop makes multiple passages through the capillary measurement section 310.

During this back-and-forth movement, the valves 251, 296, and 298 are closed.

This step 336 comprises a plurality of sequences consisting of an outward movement step 336a, in which the stream of drops circulates in the channel 252 towards the outlet 252b, and a return step 336b, in which the stream of drops circulates in the channel 252 towards the inlet 252a.

In the outward movement step 336a, the valve 284 is opened, such that the carrier fluid $f_p$ contained in the reservoir 272 is kept at the pressure $P_0$ by the pressurisation means 280. Furthermore, the valve 282 is closed, and the second pressurisation means 286 are controlled to apply a pressure P, greater than $P_0$, to the reservoir 270. The valves 274 and 276 are also open, such that a positive pressure differential is created between the reservoir 270 and the reservoir 272, causing the carrier fluid to move from the reservoir 270 to the reservoir 272 via the channel 252.

In fact, the application of the pressure P to the reservoir 270 thus generates a flow of carrier fluid $f_p$ from this reservoir 270 to the cross junction 260. This flow of carrier fluid $f_p$ is guided towards the detection channel 252, whereby the valve 296 prevents the flow from moving towards the waste reservoir W2.

This flow thus causes a displacement of the stream of drops in the channel 252 from the inlet 252a to the outlet 252b, whereby the entire stream is kept in the channel 252.

During this displacement, the stream of drops pushes the carrier fluid out, whereby the valves 276 and 298 guide the flow of carrier liquid out of the channel 252 into the reservoir 272.

In the return step 136b, the valve 282 is opened, such that the carrier fluid $f_p$ contained in the reservoir 270 is kept at the pressure $P_0$ by the pressurisation means 278. Furthermore, the valve 284 is closed, and the second pressurisation means 286 are controlled to apply a pressure P, greater than $P_0$, to the reservoir 272. The valves 274 and 276 are also open, such that a positive pressure differential is created between the reservoir 272 and the reservoir 270, causing the carrier fluid to move from the reservoir 272 to the reservoir 270 via the channel 252.

The application of the pressure P to the reservoir 272 thus generates a flow of carrier fluid $f_p$ from this reservoir 272 to the T connector 268. This flow of carrier fluid $f_p$ is guided towards the detection channel 252, whereby the valve 298 prevents the flow from moving towards the waste reservoir W2.

This flow thus causes a displacement of the stream of drops in the channel 252 from the outlet 252b to the inlet 252a, whereby the entire stream is kept in the channel 252.

During this displacement, the stream of drops pushes the carrier fluid out of the channel 252, whereby the valves 296, 251 and 274 guide the flow of carrier liquid out of the channel 252 into the reservoir 270.

During each of the outward 336a and return 336b steps, each of the drops passes through the capillary measurement section 310.

The source 300 constantly emits a coherent incident beam 311 directed towards the capillary measurement section 310 after reflecting off of at least one mirror 312 and after being focused by a lens 314.

The detector 302 receives the output beam 316 resulting from the passage of the incident beam through the capillary measurement section 310, and determines, based on the output beam 316, the optical density of the fluid passing through the capillary measurement section 310.

In particular, when a drop passes through the capillary measurement section 310, the detector thus determines the content of the drop, in particular its biomass.

Additionally, when a drop passes through the capillary measurement section 310, it fluorescently emits a reflected beam 318, which is transmitted through the mirror 312 and received by the detector 304. The detector 304 thus detects the passage of each drop through the capillary measurement section 310.

In these outward and return passes, each drop is labeled based on its position in the stream.

In the step 336, the stream remains entirely in the channel 202, such that it is theoretically possible to carry out as many measurements over time as is necessary on each of the drops.

The storage and detection unit 250 thus allows for simultaneous detection and referencing of every drop during its multiple passages through the channel 252 and monitoring of the reactions taking place in each drop over time.

For example, when carrying out multiple antibiotic resistance tests, the bacterial and antibiotic concentrations in each drop is determined at least once every 15 minutes.

Thus, for each concentration of each antibiotic, at the end of the experiment, a number of kinetic data are available that indicate the effect of the antibiotic on the bacteria at this concentration. Such measurements allow for the minimum inhibiting concentration of each antibiotic, corresponding to the minimum concentration at which the bacteria do not develop in the culture medium.

At the end of the experiment, in a step 340, the stream of drops is evacuated from the channel 252 via the branch 266, towards the waste reservoir W2.

To this end, the valves 296, 282, and 284 are closed whilst the valves 274 and 298 are open.

The second pressurisation means 286 are controlled to apply a pressure P to the reservoir 270, generating a flow of carrier liquid $f_p$ from the reservoir 270 to the cross junction 260, and then through the channel 252 from the inlet 252a to the outlet 252b until the entire stream flows via the valve 298 into the waste reservoir W2.

During this displacement, the stream of drops pushes the carrier fluid out, whereby the valves 276 and 298 guide the flow of carrier liquid out of the channel 252 into the reservoir 272.

The method according to the invention thus allows for precise, reproducible, automated study of the growth kinetics of aerobic and anaerobic bacteria based on between one and several thousand parameters at once.

It is to be understood that the exemplary embodiment described above is by no means limiting.

Additionally, the method according to the invention is not limited to the performance of antibiotic resistance tests.

The invention claimed is:

1. A method of monitoring a reaction in a reaction mixture, during the culture of microorganisms in a culture medium, wherein in the method comprises the following steps:
   a) filling a capillary reaction tube with a carrier fluid that is immiscible with the reaction mixture;
   b) injecting, by means of a capillary injection tube, an individual drop of reaction mixture comprising microorganisms in the capillary reaction tube, into the immiscible carrier fluid;
   c) circulating the carrier fluid so that the drop of reaction mixture is moved relative to the capillary injection tube;
   e) repeating steps b) and c) to create an ordered succession of drops of reaction mixture in the carrier fluid to form a plurality of reactors, each reactor being an individual drop of reaction mixture comprising microorganisms in the carrier fluid;
   f) measuring by a reaction monitoring detector at least one value of at least one parameter representative of a reaction in each individual drop of the succession of drops of reaction mixture in the carrier fluid and of the quantity of microorganism present in each individual drop;
   g) introducing the succession of drops into a recirculator tube comprising a downstream portion positioned downstream of the reaction monitoring detector, and an upstream portion disposed upstream of the reaction monitoring detector, the drops flowing through the recirculator tube and being discharged from said upstream portion, thereby recirculating the succession of drops of reaction mixture in the carrier fluid by making each drop of reaction mixture in the carrier fluid pass repeatedly in the recirculation tube in a single direction in front of the reaction monitoring detector and measuring, by said reaction monitoring detector, for each individual drop of the succession of drops of reaction mixture in the carrier fluid, successive values of said at least one parameter representative of the reaction and the quantity of microorganism present in said individual drop, over time.

2. The method of monitoring a reaction in a reaction mixture as claimed in claim 1, further comprising, after step c) and before step e), a step d) comprising injection, into the carrier fluid, of a drop of a separating fluid, immiscible with the carrier fluid and immiscible with the reaction mixture, so that at least one drop of separating fluid is interposed between two individual drops of reaction mixture in the carrier fluid and prevents their coalescence.

3. The method of monitoring a reaction in a reaction mixture as claimed in claim 1, in which measurement is carried out by an optical method selected from the group consisting of measurements of absorbance, of diffusion, and of fluorescence, or by an electrical measurement comprising measuring impedance.

4. The method of monitoring a reaction in a reaction mixture as claimed in claim 1, further comprising, after step e), a step f1) of recovery of at least one individual drop of reaction mixture in the carrier fluid of interest by aspiration of said individual drop of reaction mixture from the carrier fluid of interest into a sampling capillary tube mounted opening into the capillary reaction tube.

5. A method for monitoring reaction kinetics in a reaction mixture between at least one component of the reaction mixture and each of a plurality of different reagents, comprising:
   generating an ordered stream of drops in a carrier fluid to form a plurality of reactors, said stream of drops comprising a series of elementary streams of drops, each elementary stream of drops being associated with at least one reagent of the plurality of reagents, whereby each drop of each elementary stream comprises said at least one reagent associated with the said elementary stream,
   circulating the ordered stream of drops repeatedly in front of a reaction monitoring detector,
   measuring, by said reaction monitoring detector, for each drop of the ordered stream of drops, successive values of at least one parameter representative of a reaction in said drop over time.

6. The method according to claim 5, wherein each elementary stream of drops comprises at least one reagent not included in an adjacent elementary stream of drops.

7. The method according to claim 5, wherein generating the ordered stream of drops comprises:
   generating a plurality of consecutive elementary streams of drops, each of which is associated with at least one reagent of the plurality of reagents, between which intermediate streams of drops are arranged, and
   suppressing with a valve the intermediate streams of drops.

8. The method according to claim 5, wherein the concentration of at least one reagent varies within at least one elementary stream of drops according to a gradient.

9. The method according to claim 5, wherein generating the ordered stream of drops includes the following steps:
   (a') generating a flow of reaction mixture,
   (b') filling a capillary reaction tube with a carrier fluid that is immiscible with the reaction mixture,
   (c') injecting an individual drop of reaction mixture in the capillary reaction tube by means of a capillary injection tube,
   (d') circulating the carrier fluid so that the drop of reaction mixture is displaced relative to the capillary injection tube,
   (f') the repetition of steps c') and d') to create an ordered stream of drops of reaction mixture in the carrier fluid.

10. The method according to claim 9, wherein generating the flow of reaction mixture comprises:
   forming a flow of reagents comprising a series of elementary reagent flows, each of which comprises at least one reagent of the plurality of reagents;
   mixing the flow of reagents with a culture medium comprising the component to form the reaction medium flow.

11. The method according to claim 10, wherein forming the flow of reagents comprises the following steps:
   ($\alpha$) generating a continuous flow of a solvent in a mixing channel;
   ($\beta$) simultaneously with step $\alpha$), injecting, by means of a capillary tube, a reagent chosen from the plurality of reagents, in the mixing channel to form an elementary reagent flow;
   ($\gamma$) repeating step $\beta$) for each of the successive reagents of the plurality of reagents.

12. The method according to claim 11, wherein forming the flow of reagents comprises, after the formation of each elementary reagent flow and before step γ), a step δ) of injecting a cleaning liquid into the mixing channel by means of a capillary tube.

13. The method according to claim 9, wherein generating the ordered stream of drops further includes, after step d') and before step f), a step e') comprising injecting into the carrier fluid of a drop of a separating fluid immiscible with the carrier fluid or the reaction mixture, such that at least one drop of separating fluid is intercalated between two reactors and prevents them coalescing.

14. The method according to claim 1, further comprising a step of referencing, using a referencing detector, each individual drop of reaction mixture in the carrier fluid and identifying each individual drop of reaction mixture in the carrier fluid uniquely in the succession of individual drops of reaction mixture in the carrier fluid, and a step of storing in a memory a position of each individual drop of reaction mixture in the carrier fluid relative to a reference reactor.

15. The method according to claim 14, further comprising a step of associating each value of the representative parameter of the reaction in each individual drop, measured by said reaction monitoring detector, to the position of said individual drop relative to the reference reactor.

16. The method according to claim 15, further comprising, for each individual drop, associating the position of said individual drop relative to the reference reactor to the successive values of the representative parameters of the reaction in said individual drop measured by said reaction monitoring detector.

17. The method according to claim 5, further comprising a step of referencing, using a referencing detector, each drop of the ordered stream of drops and identifying each drop of the ordered stream of drops uniquely in the ordered stream of drops, and a step of storing in a memory a position of each drop of the ordered stream of drops relative to a reference reactor.

18. The method according to claim 17, further comprising a step of associating each value of the at least one parameter representative of the reaction in each drop, measured by said reaction monitoring detector, to the position of said drop relative to the reference reactor.

19. The method according to claim 17, further comprising, for each drop, associating the position of said drop relative to the reference reactor to the successive values of the at least one parameter representative of the reaction in said drop measured by said reaction monitoring detector.

* * * * *